United States Patent [19]
Cagle et al.

[11] Patent Number: 5,631,004
[45] Date of Patent: *May 20, 1997

[54] USE OF SUSTAINED RELEASE ANTIBIOTIC COMPOSITIONS IN OPHTHALMIC SURGICAL PROCEDURES

[75] Inventors: Gerald D. Cagle, Fort Worth; Tai-Lee Ke, Grand Prairie; Barry A. Schlech; Ole J. Lorenzetti, both of Fort Worth, all of Tex.

[73] Assignee: Alcon Laboratories, Inc., Fort Worth, Tex.

[*] Notice: The term of this patent shall not extend beyond the expiration date of Pat. No. 5,369,095.

[21] Appl. No.: 129,924

[22] Filed: Sep. 30, 1993

[51] Int. Cl.⁶ .......................... A61K 31/70; A61K 31/74
[52] U.S. Cl. .......................... 424/78.04; 514/23; 514/82
[58] Field of Search .................. 514/82, 23; 424/78.04

[56] References Cited

U.S. PATENT DOCUMENTS

| | | | |
|---|---|---|---|
| 4,271,143 | 6/1981 | Schoenwald et al. | 424/78 |
| 4,343,787 | 8/1982 | Katz | 424/78 |
| 4,540,408 | 9/1985 | Lloyd | 604/294 |
| 4,882,150 | 11/1989 | Kaufaman | 424/428 |
| 5,098,997 | 3/1992 | Anilionis et al. | 530/350 |
| 5,221,696 | 6/1993 | Ke et al. | 514/786 |
| 5,369,095 | 11/1994 | Kee et al. | 514/24 |

OTHER PUBLICATIONS

Schoenwald, "Corneal Penetration Behavoir of B–Blocking Agents I: Physiochemical Factors", *Journal of Pharmaceutical Science*, vol. 72, pp. 1266–1272 (1983).

Hobden, J. A., et al, "Quinolones in Collagen Shields to Treat Aminoglycoside-resistant Pseudomonal Keratitis", *Inves. Ophthalmol, Vis. Sci.*, vol. 31. No. 11, pp. 2241–2243 (Nov. 1990).

Mondino, B. J., "Collagen Shields", *American Journal of Ophthalmology*, vol. 112, No. 5, pp. 587–590 (Nov. 1991).

*Primary Examiner*—Elli Peselev
*Attorney, Agent, or Firm*—Gregg C. Brown

[57] ABSTRACT

An improved method of sterilizing the field of surgery prior to an ophthalmic surgical procedure is described. The invention eliminates the need for painful and potentially traumatic injections of antibiotics by utilizing sustained release compositions which allow the antibiotics contained therein to penetrate deeply into the eye, thereby ensuring a sterile field of surgery during intraocular surgical procedures. The compositions may also be utilized to prevent post-surgical infections.

4 Claims, No Drawings

USE OF SUSTAINED RELEASE ANTIBIOTIC COMPOSITIONS IN OPHTHALMIC SURGICAL PROCEDURES

BACKGROUND OF THE INVENTION

The present invention relates to sustained release pharmaceutical compositions containing one or more antibiotics. The invention is also directed to the use of such compositions to sterilize the tissues in the area of surgery (i.e., the "surgical field" or "field of surgery") prior to a surgical procedure and to prevent post-surgical infections.

Ophthalmic surgical procedures currently involve the topical application of betadine solution to the eyelid and other tissues adjacent to the eye prior to surgery. The preoperative procedures may also include topical instillation of argyrol to facilitate removal of mucus and other debris present on the cornea and conjunctiva. However, the foregoing procedures do not result in sterilization of the ophthalmic tissues which form the site of the surgery (e.g., the cornea, sclera or various other ophthalmic tissues).

Antimicrobial agents such as the aminoglycosides, penicillins and cephalosporins, being relatively insoluble in lipids, penetrate the eye poorly after systemic administration. Therefore, the surgical field is currently sterilized by subconjunctival injection of any one of various antibiotics. The most commonly used drug in subconjunctival injection is gentamicin (about 30 mg per injection). This method involves the insertion of a 20-gauge needle into the subconjunctival space, taking care not to pierce the conjunctiva; 0.1 ml to 1.0 ml of antibiotic is injected. This technique permits significant antibiotic to enter the corneoscleral limbus near the subconjunctival injection site. However, such injections present a significant risk of injury to ophthalmic tissues of performed improperly. Even when proper procedures are followed, such injections are painful and inherently involve at least some undesirable trauma due to the passing of the hypodermic needle through very delicate. ophthalmic tissues. In addition, subconjunctival injections of antibiotics can result in nonuniform concentrations of the antibiotics in the cornea, and the concentrations attained may be inadequate. For example, the maximum gentamicin concentration attained in the aqueous humor of rabbits from subconjunctival injection is 8.8 ug/g. Although a concentration of 8.8 ug/g would be effective against some bacteria, a significantly higher concentration is required for more resistant strains. Still another problem is the fairly recent development of bacterial resistance to aminoglycoside antibiotics.

The intravenous ("IV") and oral dosage of quinolones have been suggested for prophylactic usage and as an alternative to subconjunctival injections. However, the maximum aqueous humor concentration from IV injection (200 mg) and oral dosage (1 g) of ciprofloxacin in humans is 0.16 ug/ml and 0.33 ug/ml, respectively, at one hour after administration. This is less than its MIC90 (0.5 ug/g). These non-ocular delivery routes are also associated with higher risks of systemic side effects. The topical application of existing antibiotic formulations is useful in cases of superficial infections, but is inadequate for the delivery of high concentrations of antibiotics to deeper eye tissues prior to surgery.

This risk of infection subsequent to ophthalmic surgery is a significant concern. The post-surgical application of an antibiotic is therefore normally desirable. However, as with the current procedures for sterilizing the ophthalmic field prior to surgery, the post-surgical administration of antibiotics by means of hypodermic injections has significant drawbacks.

Accordingly, improved methods of sterilizing ophthalmic tissues prior to surgery and preventing post surgical infections are needed.

SUMMARY OF THE INVENTION

The present invention is directed to the use of sustained release antibiotic compositions to sterilize the field of surgery prior to ophthalmic surgical procedures and prophylactically treat post-surgical infections. The invention has significant advantages relative to prior methods of sterilizing the field of surgery and prophylactically treating post-surgical infections. The principal advantages are as follows: (1) the drug is more evenly distributed; (2) a MIC is achieved fairly rapidly; (3) the drug has a longer residence time in the cornea and other ophthalmic tissues; and (4) the pain, trauma and inherent hazards of hypodermic injections are avoided.

The compositions of the present invention comprise one or more antibiotics in a sustained-release vehicle. The preferred antibiotics are quinolones (e.g., ciprofloxacin). The preferred vehicle is a viscous gel. Other types of vehicles which provide for a sustained release of the antibiotics, such as a solid insert which is placed in the cul-de-sac of the eye and then gradually erodes as it is bathed with ocular fluids, may also be used.

It has been found that the compositions of the present invention enable potent, ophthalmically acceptable antibiotics to penetrate the anterior chamber of the eye in concentrations that are bactericidal relative to most gram-negative and gram-positive organisms. The sustained-release of antibiotics from the compositions of the present invention enables the therapeutic objectives of sterilizing the surgical field and preventing post-surgical infections to be accomplished by means of a single application of the compositions topically to the eye.

DESCRIPTION OF PREFERRED EMBODIMENTS

The antibiotics which may be used in the present invention include all antibiotics which: (1) have potent, broad activity against ophthalmic pathogens; (2) are at least partially water soluble; (3) are capable of penetrating the corneal epithelium; and (4) are nontoxic to ophthalmic tissues. Antibiotics which satisfy the foregoing criteria are referred to herein as being a "potent, ophthalmically acceptable antibiotic". The potent, ophthalmically acceptable antibiotics utilized in the present invention preferably have a minimum inhibitory concentration ("MIC") against common ophthalmic pathogens of four micrograms per milliliter (4 mcg/ml), or less. Also, the minimum bactericidal concentration ("MBC") of these antibiotics, relative to specified ophthalmic pathogens, is preferably no more than two times greater than the minimum inhibitory concentration thereof.

The most preferred antibiotics are quinolones. Aminoglycosides are also preferred. Both of these classes of antibiotics are well known. Representative examples of antibiotics from each of these classes are presented below:

| Quinolones | Aminoglycosides |
| --- | --- |
| Ciprofloxacin | Gentamicin |
| Ofloxacin | Tobramycin |
| Norfloxacin | |

Other classes of antibiotics which may be utilized include cephalosporins and penicillins. Further examples of antibiotics which may be used are listed below:

| | | |
|---|---|---|
| Amikacin | Cephalothin | Methicillin |
| Ampicillin | Chloramphenicol | Oxacillin |
| Carbenicillin | Clindamycin | Penicillin GK |
| Cefazolin | Colistin | Piperacillin |
| Cefoxitin | Erythromycin Lactobionate | Streptomycin |
| Ceftazidime | Imipenem | Ticarcillin |
| Cefotaxime | Kanamycin | Vancomycin |

The concentration of antibiotic utilized in the compositions of the present invention will vary depending on the intended use of the compositions (i.e., sterilization of the surgical field or prevention of post-surgical infections), and the relative antimicrobial activity of the specific antibiotic selected. The antimicrobial activity of antibiotics is generally expressed as the minimum concentration required to inhibit the growth of a specified pathogen. This concentration is also referred to as the "minimum inhibitory concentration" or "MIC". The term "MIC90" refers to the minimum concentration of antibiotic required to inhibit the growth of ninety percent (90%) of a population of multiple strains of a microorganism. The concentration of an antibiotic required to totally kill a specified population of bacteria or other pathogens is referred to as the "minimum bactericidal concentration" or "MBC".

The minimum inhibitory concentrations of some of the preferred antibiotics of the present invention, relative to a specific strain of pseudomonas aeruginosa (i.e., Strain 4N3422), are presented in the following table:

| Antibiotic | MIC (µg/mL) |
|---|---|
| Amikacin | 8 |
| Ceftazidime | 1 |
| Cefotaxime | 32 |
| Cefoxitin | >32 |
| Ciprofloxacin | <0.125 |
| Gentamicin | >8 |
| Imipenem | 1 |
| Norfloxacin | <0.5 |
| Piperacillin | <8 |
| Tobramycin | >8 |
| Ticarcillin | 32 |

The activity of antibiotics against pseudomonas aeruginosa is particularly important in the present invention, because ophthalmic infections involving pseudomonas aeruginosa represent an extremely serious condition which may ultimately result in the loss of the affected eye. The activities of three particularly preferred antibiotics, ciprofloxacin, gentamicin and tobramycin, relative to multiple strains of pseudomonas aeruginosa and other ophthalmic pathogens are presented in the following table:

| | MIC 90 (µg/ml) | | |
|---|---|---|---|
| | Ciprofloxacin | Gentamicin | Tobramycin |
| *Staph. aureus* | 0.5 | 12.5 | 6.3 |
| *Staph. epidermidis* | 0.4 | 12.5 | 56.0 |
| *Hemo. influenzae* | 0.015 | 0.8 | 13.4 |
| *Strep. pneumoniae* | 2.0 | 50.0 | 34.5 |
| *P. aeruginosa* | 0.5 | 8.0 | 20.0 |

The appropriate concentration for specific antibiotic/vehicle combinations can be readily determined by persons skilled in the field of ophthalmic pharmaceuticals. More specifically, an mount of antibiotic sufficient to provide a concentration in the aqueous humor and lacrimal fluid equal to or greater than the MIC90 level for the selected antibiotic, relative to gram-negative and gram-positive organisms, will be required. Such amount is referred to herein as "an antimicrobial effective amount". In general, the compositions of the present invention will contain one or more antibiotics in a concentration of from about 0.03 to about 30.0 percent by weight, based on the total weight of the compositions ("wt. %").

The above-described antibiotics are contained in ophthalmic pharmaceutical compositions which provide for sustained release of the antibiotic. The degree of sustained release required may vary depending on the antibiotic selected. However, a residence time of at least five to ten minutes, preferably ten minutes or more, will typically be required. The composition may be in the form of a solid insert which gradually erodes when placed in the cul-de-sac of the eye, or a viscous gel which slowly dissolves when contacted with the lacrimal fluid.

The viscous gels utilized in the present invention will generally have a viscosity in excess of 1,000 cps in order to ensure an adequate residence time in the eye. Any synthetic or natural polymer which is capable of forming a viscous or a solid insert may be utilized. In addition to having the physical properties required to form a viscous gel or solid insert, the polymers must also be compatible with tissues of the eye. The polymers must also be chemically and physically compatible with the above-described antibiotics and other components of the compositions. Polymers which satisfy the foregoing criteria are referred to herein as "ophthalmically acceptable viscous polymers". Examples of suitable polymers include:

natural polysaccharides and gums, such as:
alginates
carrageenan
guar
karaya
locust bean
tragacanth
xanthin
Synthetic polymers, such as:
agarose
Carbopol®
carboxymethylcellulose
hydroxyethylcellulose
hydroxypropylcellulose
hydroxypropylmethylcellulose
methylcellulose
polyvinyl alcohol
polyvinyl pyrrolidone In addition, proteins and synthetic polypeptides that form viscous gels and are ophthalmically acceptable can be used to provide better bioavailability. Typically, proteins that can be used include: gelatin, collagen, albumin and casein.

Polymers which have high molecular weights and, most importantly, physical properties which mimic the physical properties of the mucous secretions found in the eye are referred to herein as being "mucomimetic". A preferred class of mucomimetic polymers are carboxy vinyl polymers having molecular weights in the range of from about 50,000 to about 6,000,000. The polymers have carboxylic acid functional groups and preferably contain between 2 and 7 carbon atoms per functional group. The gels which form during preparation of the ophthalmic polymer dispersion have a viscosity between about 1,000 to about 300,000 centipoise (cps). Suitable carboxy vinyl polymers include those called Carhomers, e.g., Carbopol® (B. F. Goodrich Co., Cleveland, Ohio). Specifically preferred are Carbopol® 934, 940, 970 and 974. Such polymers will typically be employed in an amount between about 0.05 and about 8.0 wt %, depending on the desired viscosity of the composition.

The solid inserts described in U.S. Pat. No. 4,540,408 (Lloyd) are also preferred; the entire contents of the Lloyd '408 patent are hereby incorporated in the present specification by reference. The solid inserts described in the Lloyd '408 patent comprise an elongated applicator having a soluble matrix element disposed at one end thereof. The soluble matrix element contains one or more drugs. The applicator also includes a soluble membrane which traverses the applicator, so as to separate the soluble matrix element from the rest of the applicator. When the end of the applicator containing the drug matrix element and soluble membrane is applied to the eye, the soluble membrane rapidly dissolves, thereby releasing the drug matrix element. The drug matrix element then slowly dissolves in the lacrimal fluid, releasing the drug into the lacrimal fluid as it dissolves.

Other types of solid inserts, such as the water soluble polymeric inserts described in U.S. Pat. No. 4,343,787 (Katz), may also be utilized. The entire contents of the Katz '787 patent are hereby incorporated in the present specification by reference.

The compositions of the present invention will preferably also include one or more agents to enhance the ocular penetration and absorption of the antibiotic. The epithelium is the main barrier to drug penetration of the cornea. It is possible to enhance the penetration of drugs through the epithelium by promoting drug partition into the epithelium, thereby enhancing the overall absorption of drugs applied topically to the eye. For example, the partition coefficient of ciprofloxacin between N-Octanol/0.1M phosphate (pH=7.0) is 0.02, which is low. Consequently, this drug has difficulty penetrating the lipophilic epithelial barrier. The use of a penetration enhancer may therefore be required in connection with certain antibiotics in order to ensure that an amount of the antibiotic sufficient to sterilize the surgical field and/or prevent post-surgical infection penetrates the cornea.

The penetration enhancer generally acts to make the cell membranes less rigid and therefore more amenable to allowing passage of drug molecules between cells. The penetration enhancers preferably exert their penetration enhancing effect immediately upon application to the eye and maintain this effect for a period of approximately five to ten minutes. The penetration enhancers and any metabolites thereof must also be non-toxic to ophthalmic tissues. Penetration enhancers which meet all of the foregoing criteria are referred to herein as "rapid acting, ophthalmically acceptable, corneal penetration enhancers". One or more penetration enhancers will generally be utilized in an amount of from about 0.01 to about 20.0 wt. %, preferably from about 0.01 to about 1.0 wt. %.

The preferred penetration enhancers are saccharide surfactants, such as dodecylmaltoside ("DDM"), and monoacyl phosphoglycerides, such as lysophosphatidylcholine. The saccharide surfactants and monoacyl phosphoglycerides which may be utilized as penetration enhancers in the present invention are known compounds. The use of such compounds to enhance the penetration of ophthalmic drugs is described in commonly assigned U.S. Pat. No. 5,221,696 and U.S. patent application Ser. No. 031,000, filed Mar. 12, 1993 (now U.S. Pat. No. 5,369,095), respectively. The entire contents of the above-identified patent and patent application are hereby incorporated in the present specification by reference.

The penetration enhancing monoacyl phosphogylcerides used in the present invention have the following structure:

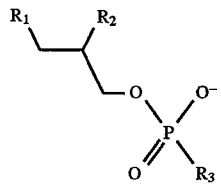

wherein one of $R_1$ and $R_2$ is hydrogen, thiol, hydroxyl, amino, lower alkyl, lower alkoxy (e.g., methyl, ethyl, methoxy or ethoxy) or alkyl sulfide and the other is an estefiified, etherified or amidified hydrophobic group, and $R_3$ is a hydrophilic group. The preferred hydrophobic groups include saturated and unsaturated aliphatic hydrocarbon groups which range from 14 to 24 carbons in length with zero to 5 double bonds. The aliphatic hydrocarbon groups can be straight or branched chain and may be substituted by one or more aromatic, cycloaliphatic or hydrophilic (e.g., hydroxyl, thiol, or amino) groups. Examples of suitable hydrophilic groups ($R_3$) include O-inositol, choline, O-choline, O-carnitine, O-$(CH_2)_3$-choline, O-glycerol and O-lysophosphatidyl-glycerol.

The preferred monoacyl phosphoglycerides are lysophospholipids, such as lysophosphatidylcholine, lysophosphatidylinositol (lysolecithin), lysocardiolipin, lysodesoxylipids, lysophosphorylipids and ∝-lyso-r-O-alkyl or O-alkenyl phospholipids such as DL-∝-Lysolecithin-r-O-hexadecyl and DL-∝-Lysolecithin-r-O-alkyl. The most preferred monoacyl phosphoglyceride is 1-acyl lysophosphatidylcholine (C18:0, C18:1, C16:0 or C16:1). The 1-acyl lysophosphatidylcholine C18:0 (lysolecithin) which is most preferred has the following structural formula:

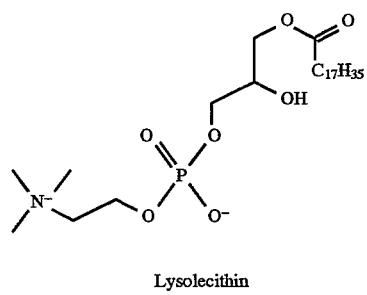

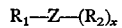

Lysolecithin

The penetration enhancing, substituted glycosides used in the present invention have the following structure:

$$R_1-Z-(R_2)_x$$

wherein:

$R_1$ is a hydrophobic group including saturated and unsaturated aliphatic hydrocarbon groups which range from 8 to 28 carbons in length with 1 to 5 double bonds, and which can be a straight or branched chain and may be substituted by one or more aromatic, cycloaliphatic or hydrophilic (e.g., hydroxyl, thiol, ester or amino) groups;

$R_2$ is a group derived from any cyclic or acyclic saccharide containing 4–7 carbons and their isomers;

X is an integer from 1–10; and

Z is an oxy (—O—),

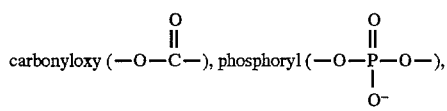

thio (—S—), or carboxamido

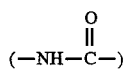

where $R_2$ is covalently bound to such group.

More specifically, $R_1$ is preferably a straight 8–18 carbon alkyl chain in hemiacetal linkage (glycoside) to the saccharide; and $R_2$ is preferably a group derived from any of a variety of isomeric saccharities containing 5 or 6 carbons. The saccharide can be, for example, an aldehyde-containing saccharide (glucose, mannose, arabinose, galaclose, xylose); a ketone-containing saccharide (fructose, xylulose, sorbose); a saccharide alcohol (sorbitol, inositol, xylitol, mannitol); a saccharide acid (glucuronic acid, neuramic acid, mannuronic acid); a deoxysaccharide (deoxy-ribose, rhamnose); or an aminosaccharide (glucosamine, galactosamine). Higher order saccharides which are covalently linked in any of a number of ways to form different isomeric structures can also be utilized. For example, disaccharides such as maltose, cellobiose, sucrose and lactose, and trisaccharides, such as raffinose, can be utilized.

The preferred penetration enhancers are alkyl chain-containing glycosides derived from maltose and glucose, wherein $R_1$ contains 8 to 18 carbons. The most preferred penetration enhancer is dodecylmaltoside (sometimes referred to herein as "DDM").

The methods and compositions of the present invention are further illustrated by the selected embodiments of the invention discussed in the following examples.

EXAMPLE 1

| Ingredient | Amount (wt. %) |
|---|---|
| Carbopol ® 934 | 1.0% |
| Ciprofloxacin HCl | 0.35% |
| Benzalkonium chloride ("BAC") | 0.006% |
| Dodecylmaltoside ("DDM") | 0.05% |
| NaOH (1N) | adjust pH to 4.8–5.0 |

This formulation may be prepared as follows. Starting with 1% Carbopol® solution (pH=3.0), slowly stir and heat the solution to 70°–80° C. (Heating is necessary in order to avoid the formation of an insoluble precipitate.) Add 0.3% ciprofloxacin into the hot solution and stir very slowly until all drugs are dissolved. After semi-cool, add 0.006% BAC and 0.05% DDM into the solution and stir slowly to avoid air bubbles. Finally, adjust pH to 5.0 with 1N NaOH to form the gel (adding NaOH extremely slowly with pipettes). The percentage of free drugs in gel formulation is 100%. No drug was found to be bound with Carbopol® material.

EXAMPLE 2

Albino rabbits were sacrificed, and within 15 minutes, the corneas were mounted and clamped between two lucite diffusing cells according to the published procedure given by Schoenwald. See: Schoenwald, "Corneal Penetration Behavior of B-Blocking Agents I: Physiochemical Factors", Journal of Pharmaceutical Science, volume 72, pages 1266–72 (1983). A volume of 7 ml glutathione bicarbonated Ringer's solution was added to the endothelial side to serve as the receiver solution. An equal volume of buffer solution containing drug with or without a penetration enhancer, lysophosphatidyl-choline ("Lyso PC"), was then added to the epithelial side to serve as the donor solution. The composition of the two donor solutions was as follows:

| | Amount (wt. %) | |
|---|---|---|
| Ingredient | Formulation A | Formulation B |
| NaCl | 0.652 | 0.652 |
| KCl | 0.0359 | 0.0359 |
| $CaCl_2.2H_2O$ | 0.0153 | 0.0153 |
| $MgCl_2.6H_2O$ | 0.0159 | 0.0159 |
| $NaH_2PO_4$ | 0.0103 | 0.0103 |
| $NaHCO_3$ | 0.2453 | 0.2453 |
| Glucose | 0.0903 | 0.0903 |
| Reduced Glutathione | 0.0092 | 0.0092 |
| Ciprofloxacin HCl | 0.03 | 0.03 |
| LysoPC | — | 0.01 |
| Water | q.s. 100 | q.s. 100 |

The corneal penetration coefficient of drug was determined based on the rate of drug appearing in the receiver solution. The results of this experiment are presented below:

| | Penetration Coefficient (cm/sec) | Permeation Increase (fold) |
|---|---|---|
| Formulation A | $2.77 \times 10^{-6}$ | |
| Formulation B | $40.62 \times 10^{-6}$ | 14.7 |

The foregoing results clearly indicate that the formulation containing 0.01 wt. % lyso PC (i.e., Formulation B) provided a much higher degree of drug penetration, compared to the control formulation, which did not include a penetration enhancer. Based on the foregoing results and other studies, it has been concluded that the above-described penetration enhancers will significantly promote the permeation of any hydrophilic antibiotic whose in vitro corneal penetration coefficient is less than $6.0 \times 10^{-5}$ cm/sec.

EXAMPLE 3

New Zealand albino rabbit eyes were selected for evaluation of ciprofloxacin with enhanced sustained vehicle. The following formulations were tested:

| Ingredient | Formulation A (solution form) Amount (wt. %) |
|---|---|
| Ciprofloxacin HCl | 0.35 |
| EDTA | 0.05 |
| BAC | 0.006 |
| NaAc | 0.03 |
| Mannitol | 4.6 |
| DDM | 0.05 |
| HPMC (E50LV) | 3.3 (viscosity 300 cps) |
| HAc | adjust pH to 4.8–5.0 |
| Water | q.s. 100 |

| Ingredient | Formulation B Amount (wt. %) | Formulation C Amount (wt. %) |
|---|---|---|
| Carbopol 934 | 1.0 | 1.0 |
| Ciprofloxacin HCl | 0.35 | 0.35 |
| BAC | 0.006 | 0.006 |
| DDM | — | 0.05 |
| NaOH (1N) | adjust pH to 4.8–5.0 | adjust pH to 4.8–5.0 |
| Water | q.s. 100 | q.s. 100 |

The route of administration was topical. The rabbits received 30 microliters of either the gel or solution formulations in both eyes. At the end of the study, the aqueous humor and cornea were collected and assayed by high performance liquid chromatography to determine the mount of drug present. The results were summarized and are listed in Tables 1 and 2 below:

TABLE 1

One and Four Hours After Dosing

|  | Drug Concentration One Hour After Dosing (µg/g) | Drug Concentration Four Hours After Dosing (µg/g) |
|---|---|---|
| Aqueous humor |  |  |
| Formulation A | 0.51 ± 0.10 | 0.21 ± 0.02 |
| Formulation B | 0.032 ± 0.020 | 0.028 ± 0.032 |
| Formulation C | 0.69 ± 0.20 | 0.27 ± 0.06 |
| Cornea |  |  |
| Formulation A | 6.45 ± 1.12 | 3.19 ± 0.50 |
| Formulation B | 1.45 ± 0.34 | 0.94 ± 0.19 |
| Formulation C | 7.90 ± 1.90 | 3.77 ± 1.75 |

TABLE 2

Additional Time Points for Enhanced Formulations

| | Drug Concentration (µg/g) Time After Dosing | | | | | | | |
|---|---|---|---|---|---|---|---|---|
| | 15' | 30' | 60' | 120' | 180' | 240' | 480' | 24 hrs |
| Agueous Humor | | | | | | | | |
| Formulation A | 0.06 | 0.33 | 0.51 | 0.52 | 0.21 | 0.21 | 0.077 | 0.002 |
| Formulation C | 0.11 | 0.28 | 0.69 | 0.42 | 0.16 | 0.27 | 0.053 | 0 |
| Cornea | | | | | | | | |
| Formulation A | 8.25 | 10.50 | 6.45 | 6.18 | 3.18 | 3.19 | 0.96 | 0.068 |
| Formulation C | 7.60 | 10.58 | 7.90 | 4.28 | 2.80 | 3.77 | 0.63 | 0.040 |

The foregoing results indicate that in normal eyes, after 30 minutes, drug levels were 10.58 micrograms/gram (ug/g) in cornea, and 0.28 ug/g in aqueous humor. The ciprofloxacin concentration in the aqueous humor reached a maximum of 0.69 ug/g at one hour after topical administration of 0.3% in a single dose. The results show that the drug has a longer duration time in the cornea for enhanced formulations (i.e., Formulations A and C). With both enhanced formulations, the drug concentration in the cornea up to eight hours after administration is still greater than its MIC90. These ocular tissue concentrations of ciprofloxacin exceeded the MIC 90 of the compound against various bacteria of ocular pathogens, such as staphylococcus aureus, staphylococcus epidermidis, and pseudomonas aeruginosa. Thus, a single application of the above-described enhanced formulations would be sufficient to sterilize the ophthalmic field prior to surgery.

What is claimed is:

1. A topical ophthalmic composition for sterilizing the ophthalmic tissues of a human or animal patient in the area of surgery prior to an ophthalmic surgical procedure or prophylactically treating bacterial infections of the eye resulting from the ophthalmic surgical procedure, comprising:

an antimicrobial effective amount of ciprofloxacin;

a carboxy vinyl polymer having a molecular weight of 50,000 to 6,000,000; and 0.01 to 1.0 wt. % of dodecylmaltoside.

2. A method of sterilizing the ophthalmic tissues of a human patient in the area of surgery prior to an ophthalmic surgical procedure, which comprises topically applying to the affected eye prior to the surgical procedure a single dose of an ophthalmic composition comprising:

an antimicrobial effective mount of ciprofloxacin;

a carboxy vinyl polymer having a molecular weight of 50,000 to 6,000,000; and 0.01 to 1.0 wt. % of dodecylmaltoside.

3. A method according to claim 2, wherein the ophthalmic surgical procedure involves the cornea.

4. A method of prophylactically treating ocular bacterial infections resulting from an ocular surgical procedure in a human or animal patient, which comprises topically applying to an eye of the patient which has undergone a surgical procedure a single dose of a composition comprising:

an antimicrobial effective amount of ciprofloxacin;

a carboxy vinyl polymer having a molecular weight of 50,000 to 6,000,000; and 0.01 to 1.0 wt. % of dodecylmaltoside.

* * * * *